United States Patent [19]

Van Ness et al.

[11] Patent Number: 5,376,529
[45] Date of Patent: Dec. 27, 1994

[54] LACTAM-CONTAINING COMPOSITIONS AND METHODS USEFUL FOR THE HYBRIDIZATION OF NUCLEIC ACIDS

[75] Inventors: Jeffrey Van Ness, Bothell; Nicolaas M. J. Vermeulen, Woodinville, both of Wash.

[73] Assignee: MicroProbe Corporation, Bothell, Wash.

[21] Appl. No.: 807,525

[22] Filed: Dec. 13, 1991

Related U.S. Application Data

[60] Division of Ser. No. 558,896, Jul. 27, 1990, Pat. No. 5,106,730, which is a continuation-in-part of Ser. No. 384,235, Jul. 24, 1989, abandoned.

[51] Int. Cl.$^5$ .............................................. C12Q 1/68
[52] U.S. Cl. ........................................ 435/6; 540/451; 540/463; 540/485; 540/526; 540/527; 546/243; 548/547
[58] Field of Search .................... 435/6, 259; 548/543, 548/546, 547; 546/243; 540/485, 526, 527, 451, 463; 935/78

[56] References Cited

U.S. PATENT DOCUMENTS 4,302,204  11/1981  Wahl et al. ............................. 435/6
4,483,920  11/1984  Gillespie et al. ........................ 435/6
4,652,517   3/1987  Scholl et al. ......................... 435/259
4,830,969   5/1989  Holmes .............................. 435/259

*Primary Examiner*—Amelia Burgess Yarbrough
*Attorney, Agent, or Firm*—Townsend and Townsend Khourie and Crew

[57] ABSTRACT

This invention relates to novel methods for the release of nucleic acids from cells in complex biological samples or specimens to prepare and make available the nucleic acid material present for a hybridization assay or for extraction. Novel methods for hybridization of nucleic acids are also presented. In particular methods are described for isolating nucleic acid from a sample containing a complex biological mixture of nucleic acid and non-nucleic acids wherein the sample is combined with a hybridization medium comprising a lactam which promotes and enables nucleic acid pairing when complementary nucleic acid is introduced. The lactam is preferably about 5 to about 70% of the hybridization medium and is most preferably 2-pyrrolidone, N-ethyl-2-pyrrolidone, N-cyclohexyl-2-pyrrolidone, N-dodecyl-2-pyrrolidone, N-methyl-2-pyrrolidone, N-hydroxyethyl-2-pyrrolidone, N-methyl-2-piperidone, 2-ϵ-caprolactam, N-methyl-2-caprolactam, 2-piperidone or N-(4-hydroxybenzyl)pyrrolidone.

5 Claims, 2 Drawing Sheets

METHOD A:

METHOD B:

METHOD C:

METHOD D:

METHOD E:

METHOD A:

METHOD B:

METHOD C:

METHOD D:

METHOD E:

METHOD F:

METHOD G:

WHERE  IS PREPARED BY METHODS A, D m = 1 TO 20

WHERE  IS PREPARED BY METHOD B

WHERE  IS PREPARED BY METHOD C

WHERE IS PREPARED AS DESCRIBED:

LACTAM-CONTAINING COMPOSITIONS AND METHODS USEFUL FOR THE HYBRIDIZATION OF NUCLEIC ACIDS

This application is a divisional of U.S. application Ser. No. 07/558,896, filed Jul. 27, 1990, now U.S. Pat. No. 5,106,750, which in turn is a continuation-in-part of U.S. application Ser. No. 07/384,235, filed Jul. 24, 1989, now abandoned which application is incorporated by reference herein.

BACKGROUND OF THE INVENTION

1. Field of the Invention

This invention relates to compositions and assay methods for the hybridization and extraction of nucleic acids. In particular, this invention relates to compositions and methods to release nucleic acids from cells in complex biological samples or specimens while simultaneously hybridizing complementary nucleic acids released during lysis. The methods are based on the use of the chemical family of compounds termed lactams, preferably pyrrolidones, which promote nucleic acid base pairing, and which are effective in the extraction and purification of nucleic acids, and, alternatively, highly sensitive assays for ribonucleic acid are also described that employ a heating step.

2. Brief Description of the Relevant Art

Organic solvents such as phenol and chloroform are traditionally used in techniques employed to isolate nucleic acid from procaryotic and eucaryotic cells or from complex biological samples. Nucleic acid isolations typically begin with an enzymatic digest performed with proteases followed by cell lysis using ionic detergents and then extraction with phenol or a phenol/chloroform combination. The organic and aqueous phases are separated and nucleic acid which has partitioned into the aqueous phase is recovered by precipitation with alcohol. However, phenol or a phenol/chloroform mixture is corrosive to human skin and is considered as hazardous waste which must be carefully handled and properly discarded. Further, the extraction method is time consuming and laborious. Marmur, *J. Mol. Biol.*, 3:208-218 (1961), describes the standard preparative procedure for extraction and purification of intact high molecular weight DNA from procaryotic organisms using enzymatic treatment, addition of a detergent, and the use of an organic solvent such as phenol or phenol/chloroform. Chirgwin et al., *Biochemistry*, 18:5294-5299 (1979) described the isolation of intact RNA from tissues enriched in ribonuclease by homogenization in GnSCN and 2-mercaptoethanol followed by ethanol precipitation or by sedimentation through cesium chloride.

Further, the use of chaotropic agents such as guanidine thiocyanate (GnSCN) are widely used to lyse and release nucleic acid from cells into solution, largely due to the fact that the chaotropic salts inhibit nucleases and proteases. However, it has proved difficult to isolate the nucleic acids from these chaotropic salt solutions due to the incompatibility of the chaotropes with ionic detergents and the inability to easily partition the nucleic acid into an aqueous phase, given such high molar concentrations of salt used and the chaotropic behavior of the salts.

Nucleic acid hybridization is a known and documented method for identifying nucleic acids. Hybridization is based on base pairing of complementary nucleic acid strands. When single stranded nucleic acids are incubated in appropriate buffer solutions, complementary base sequences pair to form double stranded stable molecules. The presence or absence of such pairing may be detected by several different methods well known in the art.

Most hybridization assays previously described involve multiple steps such as the hybridization technique described by Dunn & Hassell in Cell, Vol. 12, pages 23-36 (1977). Their assay is of the sandwich-type whereby a first hybridization occurs between a "target" nucleic acid and a "capture" nucleic acid probe which has been immobilized on a solid support. A second hybridization then follows where a "signal" nucleic acid probe, typically labelled with a radioactive isotope, hybridizes to a different region of the immobilized target nucleic acid. The hybridization of the signal probe may then be detected by, for example, autoradiography.

Ranki et al. in U.S. Pat. Nos. 4,486,539 and 4,563,419 describe sandwich-type assays which first require steps to render nucleic acids single stranded and then the single stranded nucleic acids are allowed to hybridize with a nucleic acid affixed to a solid carrier and with a nucleic acid labelled with a radioisotope. Thus, the Ranki et al. assay requires the nucleic acid to be identified or targeted in the assay to be first rendered single stranded.

One approach to dissolving a biological sample in a chaotrope solution and performing molecular hybridization directly upon the dissolved sample is described by Thompson and Gillespie, "Analytical Biochemistry," 163:281-291 (1987). See also PCT Application US87/01023, Feb. 5, 1986. Cox et al. have also described the use of GnSCN in methods for conducting nucleic acid hybridization assays and for isolating nucleic acid from cells (European Application No. 84302865.5, May 12, 1984).

Bresser, Doering and Gillespie, "DNA," 2:243-254 (1983), reported the use of NaI, and Manser and Gefter, *Proc. Nat'l. Acad. Sci. USA*, 81:2470-2474 (1984) reported the use of NaSCN to make DNA or mRNA in biological sources available for trapping and immobilization on nitrocellulose membranes in a state which was suitable for molecular hybridization with DNA or RNA probes.

Hybridization media and extraction solutions which avoid the problems encountered with the use of chaotropic agents and toxic organic solvents, but which also yield sensitive assays would be desirable. Further, procedures which minimize the handling of reagents and samples would be advantageous.

SUMMARY OF THE INVENTION

This invention relates to novel methods for the release of nucleic acids from cells in complex biological samples or specimens to prepare and make available the nucleic acid material present for a hybridization assay or for extraction. Novel methods for hybridization of nucleic acids are also presented. In particular, methods are described for the hybridization of nucleic acid from a sample suspected of containing a target nucleic acid of interest wherein the sample is combined with a hybridization medium comprising a lactam which promotes and enables nucleic acid pairing when a nucleic acid complementary to the target nucleic acid is introduced. The extent of hybridization of the complementary nucleic acid to the target nucleic acid is then determined.

The concentration of the lactam is preferably about 5 to about 70% of the hybridization medium and is most preferably 2-pyrrolidone, N-ethyl-2-pyrrolidone, N-cyclohexyl-2-pyrrolidone, N-dodecyl-2-pyrrolidone, N-methyl-2-pyrrolidone, N-hydroxyethyl-2-pyrrolidone, N-methyl-2-piperidone, 2-ε-caprolactam, N-methyl-2-caprolactam, 2-piperidone (or 2-δ-valerolactam) or N-(4-hydroxybenzyl)pyrrolidone.

One advantage to these hybridization methods is that hybridization may be done completely at room temperature and in one easy step with all reagents precombined. This is particularly true if open regions of ribosomal RNA (rRNA) are used as the target nucleic acids.

The lactams used in the present invention are of a very low order toxicity and are not corrosive to human tissue. Also, when used in extraction procedures preceding hybridization they are useful in removing background interference. They retain most of the solvent properties of phenol or phenol/chloroform and are uniquely suited to the application of nucleic acid isolation and/or fractionation of biological macromolecular complexes. When used in extraction procedures, they are substantially less expensive than the commonly employed organic solvents. Further, the use of lactams avoids problems relating to the incompatibility of chaotropes with ionic detergents during isolation of nucleic acids from chaotropic salt solutions.

Alternatively, highly sensitive hybridization methods for ribonucleic acid are described wherein the sample containing the target ribonucleic acid is heated to a temperature of about 60°–100° C.

DETAILED DESCRIPTION

Figure 1A:
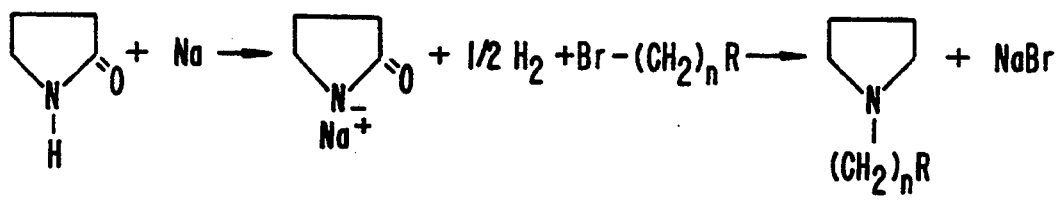
FIGS. 1A and 1B illustrate various known synthetic pathways for the production of lactams.
Figure 1A:
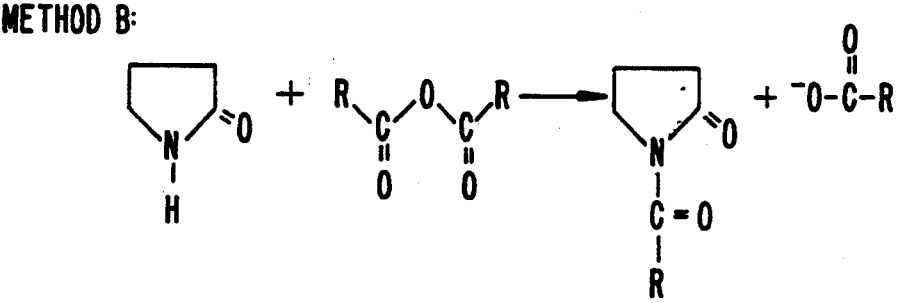
Figure 1A:
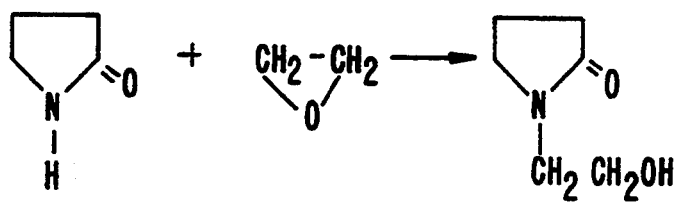
Figure 1A:
Figure 1A:
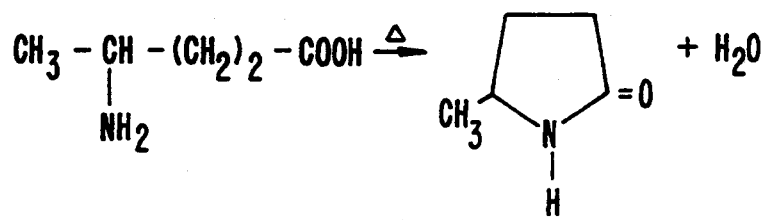
Figure 1B:
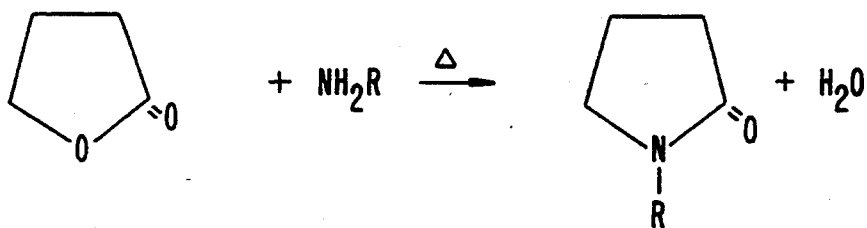
Figure 1B:
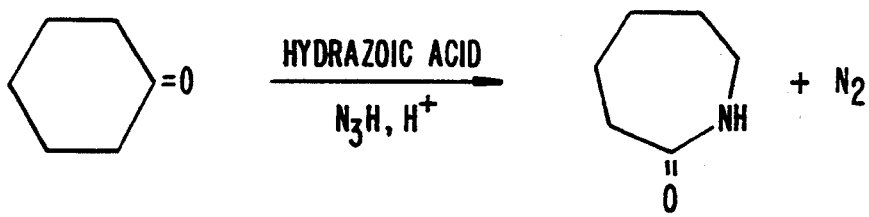
Figure 1B:
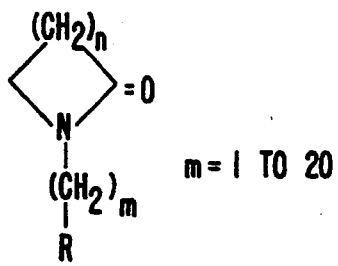
Figure 1B:
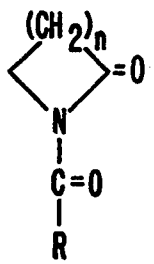
Figure 1B:
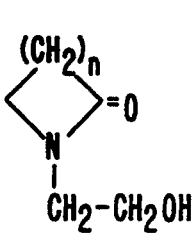
Figure 1B:
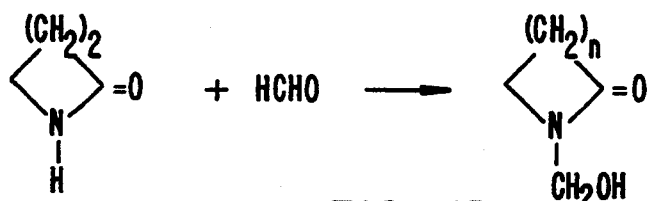

This invention relates to novel means and methods for releasing nucleic acids from a complex biological mixture containing nucleic acids and non-nucleic acids and promoting nucleic acid pairing. Highly sensitive hybridization assays are also described. The methods of the present invention enable one to easily process a biological sample containing nucleic acids by promoting the lysis of cells in the sample and promoting the hybridization of nucleic acids suspected of being present in the cells. The methods of the present invention further enable one to readily assay for a nucleic acid suspected of being present in cells, i.e., a target nucleic acid. Such methods include lysing the cells in a hybridization medium comprising a lactam, contacting the lysate under hybridization conditions with a nucleic acid having a nucleotide sequence substantially complementary to a sequence suspected to be present in the cells, and determining the extent of hybridization.

The "target nucleic acid" means the nucleotide sequence of deoxyribonucleic acid (DNA), ribonucleic acid (RNA) or ribosomal ribonucleic acid (rRNA) whose presence is of interest and whose presence or absence is to be detected for in the hybridization assay. The nucleic acid sample of interest will be one which is suspected of containing a particular target nucleic acid, such as one known to be associated with a particular microorganism, whose presence or absence is of interest. The target nucleic acid may be provided in a complex biological mixture of nucleic acid (RNA, DNA and/or rRNA) and non-nucleic acid.

The target nucleic acids of primary preference are RNA molecules and, in particular, open regions of rRNA which have minimal secondary or tertiary interactions with adjacent nucleotides, such as on the 16s or 23s rRNA as described in commonly assigned U.S. patent application Ser. No. 142,106, which is incorporated by reference herein. If target nucleic acids of choice are double stranded or otherwise have significant secondary and tertiary structure, they may need to be heated prior to hybridization. In this case, heating may occur prior to or after the introduction of the nucleic acids into the hybridization medium containing the lactam. It may also be desirable in some cases to extract the nucleic acids from the complex biological samples prior to the hybridization assay to reduce background interference by any methods known in the art. Particularly preferable are those extraction procedures utilizing lactams which are disclosed in commonly assigned U.S. patent application Ser. No. 07/384,367 filed Jul. 24, 1989, now U.S. Pat. No. 5,124,444 which is incorporated by reference herein.

The hybridization and extraction methods of the present invention may be applied to a complex biological mixture of nucleic acid (RNA and/or DNA) and non-nucleic acid. Such a complex biological mixture includes a wide range of eucaryotic and procaryotic cells, including protoplasts; or other biological materials which may harbor polynucleotide target nucleic acids. The methods are thus applicable to tissue culture animal cells, animal tissue (e.g., heart, liver or brain, homogenized in lysis buffer), blood cells, reticulocytes, lymphocytes, plant cells or other cells sensitive to osmotic shock and cells of bacteria, yeasts, viruses, mycoplasmas, protozoa, rickettsia, fungi and other small microbial cells and the like. The assay and isolation procedures of the present invention are useful, for instance, for detecting non-pathogenic or pathogenic microorganisms of interest. By detecting specific hybridization between nucleotide probes of a known source and nucleic acids resident in the biological sample, the presence of the microorganisms may be established.

The nucleic acid sample to be assayed is combined with a hybridization medium comprising a lactam. Lactams are a class of a group of organic cyclic compounds containing the —NH—CO— group in the ring. Such compounds are typically formed by the elimination of water from the amino and carboxyl groups of a noncyclic compound. The particular substituents on the lactam ring are not critical to this invention. It is, however, important that the lactam maintain hydrogen bonding capacity and water solubility. Thus, substituents of more than eight carbons, for example, would be less preferred than substituents with less than eight carbons which would be more water soluble. This is especially true if the preferred substituents contain additional polar groups.

Preferably, the lactam will be of the general formula including racemic mixtures and optically active isomers:

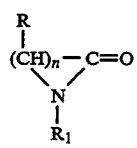

wherein n=3 to 8 (with the total number of R substituents being 3 to 8), and $R_1$ in selected from the group consisting of:
  hydrogen,
  alkyl of 1 to 20 carbons,
  aryl of 6 to 10 carbons,
  arylalkyl of 7 to 20 carbons,
  hydroxyarylalkyl of 7 to 20 carbons,
  alkylcarboxyamide of 1 to 20 carbons,
  N-mono-substituted alkylcarboxyamide,
  N, N-dialkyl-substituted alkylcarboxyamide,
  alkylcarboxylate of 2 to 20 carbons,
  acyl of 2 to 20 carbons,
  cycloalkane of 4 to 20 carbons,
  hydroxyalkyl,
  and cyanoalkyl;
and where the R substituents can be the same or different and selected from a group consisting of hydrogen, halogen and alkyl of 1 to 5 carbons such that the total carbon number for all R substituents does not exceed 20; with the further provision that the total carbon number of the $R_1$ substituent does not exceed 20 and where at least one R designated substituent is hydrogen.

Pyrrolidones, piperidones and caprolactams are lactams which are particularly preferred. The lactams which are preferred also include those where n=3 to 6, where at least one R substituent is methyl, where the $R_1$ substituent and all of the R substituents are hydrogen, where the $R_1$ substituent is other than hydrogen and the R substituents are both hydrogen, where the $R_1$ substituent is a cycloalkane of 4 to 7 carbons, where the $R_1$ substituent is —$CH_2$—$CH_2OH$, where the $R_1$ substituent is —$CH_2$—$CH_3$, where the $R_1$ substituent is methyl, or where the $R_1$ substituent is dodecyl. Examples of these preferred lactams which are most preferred are 2-pyrrolidone, N-methyl-2-pyrrolidone, N-hydroxyethyl-2-pyrrolidone, N-cyclohexyl-2-pyrrolidone, N-dodecyl-2-pyrrolidone, N-ethyl-2-pyrrolidone, N-methyl-2-piperidone, 2-ε-caprolactam, N-methyl-2-caprolactam, 2-piperidone (or 2-δ-valerolactam) and N-(4-hydroxybenzyl)pyrrolidone. These are commercially available from the GAF Chemicals Corporation (a subsidiary of GAF Corporation, Wayne, N.J.) and/or Aldrich Chemical Company (Milwaukee, Wis.).

Alkyl refers to an aliphatic hydrocarbon radical, —$(CH_2)_nCH_3$, either branched or unbranched such as methyl, ethyl, n-propyl, isopropyl, n-butyl, isobutyl, sec-butyl, tert-butyl, dodecyl or the like.

Aryl refers to a radical derived from an aromatic hydrocarbon by removal of one hydrogen atom such as phenyl, α-napthyl, β-napthyl, biphenyl, anthryl and the like.

Arylalkyl, —$(CH_2)_n$—Ar, refers to an alkyl radical as defined above joined to an aryl radical.

Alkylcarboxyamide refers to a radical, —$(CH_2)_n$—$CONH_2$.

Hydroxyarylalkyl refers to an arylalkyl radical where the aryl radical is an hydroxyaryl.

N-mono-substituted alkylcarboxyamide refers to a radical,

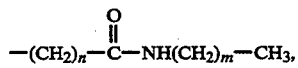

where n=10 to 20 carbons and m=1 to 5 carbons.

N,N-dialkyl-substituted alkylcarboxyamide refers to a radical

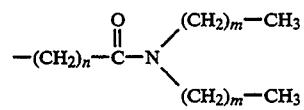

where each alkyl can be the same or different and where n=10 to 20 carbons and m=1 to 5 carbons.

Alkylcarboxylate refers to a radical —$(CH_2)_nCOO^-$, where n preferably=1 to 19 carbons.

Acyl includes any organic radical derived from an organic acid, such as a carboxylic acid by elimination of the hydroxyl group. It is represented by the formula $R_6$—CO, wherein $R_6$ can be as defined in U.S. Pat. No. 4,665,067 at column 2, line 31 through column 12, line 32, which is incorporated by reference herein. It is preferred that $R_6$ be an alkyl of 1 to 20 carbons or a cycloalkyl.

Hydroxyalkyl refers to a radical —$(CH_2)_nOH$, where n=1 to 20.

Cycloalkane or cycloalkyl refers to a radical of a saturated hydrocarbon in a ring structure such as cyclopropyl, cyclobutyl, cyclopentyl, cyclohexyl, cycloheptyl, adamantyl and the like.

Cyanoalkyl refers to a radical of a cyano group, having the formula —C≡N joined to an alkyl group, as defined above.

Unless otherwise stated, all number ranges are inclusive of the stated range (e.g., 1 to 5 carbons, includes 1 and 5 carbons).

Halogen refers to chlorine, bromine, iodine or fluorine.

Various pyrrolidone derivatives may be prepared as described in Kirk-Othmer Encyclopedia of Chemical Technology, 19:510–518 (1982), incorporated by reference herein, or as follows:

Alkali metal derivatives of pyrrolidone are readily formed by reaction with metal or from concentrated caustic soda and 2-pyrrolidone in acetone solution as described in "Acetylene Chemistry," J. W. Reppe P. B. Report, 18–852-s, C. A. Meyer & Co., Inc., New York, N.Y. (1949), 210 pp., incorporated by reference herein. Such procedure permits reaction with substituted alkyl, aryl or arylalkyl halides without opening the lactam ring, to give N-alkyl, N-aryl or N-arylalkyl pyrrolidones. See Method A on FIG. 1A. The latter two can be nitrated without rupture of the lactam ring and alkyl, hydroxy, alkoxy, or halogen substitution is also possible. N-octyl-2-pyrrolidone and N-dodecyl-2-pyrrolidone are synthesized in this manner and belong to the N-alkyl-2-pyrrolidone family. N-methyl-2-pyrrolidone, the lactam of 4-methylaminobutyric acid, is synthesized using the Reppe chemistry described above. Acylated lactams can also be chlorinated and brominated at elevated temperatures under the influence of light.

Lactams can react with the following reagents:
a) Acid anhydrides or chlorides result in formation of N-acyl lactams; for example acetic anhydride forms from N-acetyl-2-pyrrolidone. See Method B on FIG. 1A.
b) N-methylol-2-pyrrolidone results from reaction of formaldehyde and 2-pyrrolidone.
c) N-(2-hydroxymethyl)-2-pyrrolidone is formed by reaction with ethylene oxide. See Method C on FIG. 1A.

Other examples of various synthesis routes are also set forth on FIG. 1. Method D on FIG. 1A shows the reaction of butyrolactone in the presence of a moderate excess of ammonia under heat to yield 2-pyrrolidone. Method F on FIG. 1B shows the same reaction using butyrolactone and alkylamine as the starting materials to yield an alkyl substituted lactam.

Method E on FIG. 1A shows that lactams are easily produced from the pyrolysis of amino acids. The reaction of hydrazoic acids with cyclic ketones yield the corresponding lactam as shown in method G on FIG. 1B. The commercially available technical grades of all pyrrolidones should be vacuum distilled prior to use with biological samples.

The lactams should be provided in concentrations in excess of 5% of the total volume of the hybridization medium or extraction solution up to a concentration of about 70%, preferably a concentration of 20% to 50%, most preferably a concentration of about 30% to 50%. The lactams may be used singly or in combination.

Solutions containing a lactam or mixtures of the lactams are capable of effectively lysing procaryotic and eucaryotic cells while simultaneously promoting specific hybridization of nucleic acid probes to released endogenous nucleic acid. The solutions need not contain any other component other than common buffers and detergents to promote lysing and solubilization of cells and nucleic acid hybridization.

If extraction procedures are employed prior to hybridization, organic solvents such as phenol and chloroform may be used in techniques employed to isolate nucleic acid. Traditionally, organic solvents, such as phenol or a phenol-chloroform combination are used to extract nucleic acid, using a phase separation. These methods may be used effectively with the lysis solutions of the present invention; however, an advantage of the methods of the present invention is that such toxic and tedious extraction methods are not necessary. The combined hybridization media or extraction solution with the complex biological mixture itself may become biphasic with the non-nucleic acid material present in the organic phase and the nucleic acid solution present in the aqueous phase. The combined solution is typically mixed and subjected to centrifugation and the nucleic acid is precipitated with ethanol.

Preferably, the hybridization medium will contain standard buffers and detergents to promote lysing of cells. A buffer such as sodium citrate, Tris HCl, PIPES or HEPES, preferably Tris-HCl at a concentration of about 0.05 to 0.1M can be used. The hybridization medium will preferably also contain about 0.05 to 0.5% of an ionic or nonionic detergent, such as sodium dodecylsulfate (SDS) or Sarkosyl (Sigma Chemical Co., St. Louis, Mo.) and between 1 to 10 mM EDTA. Other additives may also be included, such as volume exclusion agents which include a variety of polar water-soluble or swellable agents, such as anionic polyacrylate or polymethacrylate, and charged saccharidic polymers, such as dextran sulfate and the like. Specificity or the stringency of hybridization may be controlled, for instance, by varying the NaCl concentration which is typically between 0 to 1M NaCl.

Chaotropic agents which disturb the secondary and tertiary structure of proteins, for example, guanidine salts such as guanidine hydrochloride (GnHCl) and thiocyanate (GnSCN), or urea, lithium chloride and other thiocyanates may be used in combination with the lactams to dissociate nucleic acids and inhibit nucleases. The use of chaotropic agents in the extraction and hybridization of nucleic acids is described in E.P. Publication No. 0 127 327, which is incorporated by reference herein.

A nucleic acid substantially complementary to the target nucleic acid will be introduced in the hybridization process. What is meant by "a nucleic acid substantially complementary to the target nucleic acid" is a polynucleotide or oligonucleotide containing naturally occurring nucleotides or their analogs, such as 7-deazaguanosine or inosine, sufficiently complementary to hybridize with the target nucleic acid such that stable and specific binding occurs between the target and the complementary nucleic acid. Therefore, the complementary nucleic acid sequence need not reflect the exact sequence of the target nucleic acid. For example, a non-complementary nucleotide fragment may be attached to a complementary nucleotide fragment or alternatively, non-complementary bases or longer sequences can be interspersed into the complementary nucleic acid, provided that the complementary nucleic acid sequence has sufficient complementarity with the sequence of the target nucleic acid to hybridize therewith forming a hybridization complex and further is capable of immobilizing the target nucleic acid to a solid support. The degree of homology required for formation of a stable hybridization complex (duplex) varies with the stringency of the hybridization medium and/or wash medium. Oligonucleotide probes to rRNA are most preferred such as those described in commonly assigned U.S. patent application Ser. No. 142,106, which is incorporated by reference herein. The complementary nucleic acid may be present in a pre-prepared hybridization media or introduced at some later point prior to hybridization.

The hybridization medium is combined with the biological sample to facilitate lysis of the cells and nucleic acid pairing. Preferably, the volume of biological sample to the volume of the hybridization medium will be about 1:10.

It is intended, and one advantage of the hybridization methods of the present invention is that they be carried out on complex biological samples. However, minor mechanical or other treatments may be considered under certain circumstances. For example, it may be desirable to clarify the lysate before hybridization such as by slow speed centrifugation or filtration or to extract the nucleic acids first as described above.

The hybridization assay of the present invention can be performed by any method known to those skilled in the art or analogous to immunoassay methodology given the guidelines presented herein. Preferred methods of assay are the sandwich assays and variations thereof and the competition or displacement assay. Hybridization techniques are generally described in "Nucleic Acid Hybridization, A Practical Approach," Ed. Hames, B. D. and Higgins, S. J., IRL Press, 1985; Gall and Pardue (1969), *Proc. Natl. Acad. Sci., U.S.A.*, 63:378–383; and John, Burnsteil and Jones (1969) Nature, 223:582–587. As improvements are made in hybridization techniques, they can readily be applied.

The sensitivity of the hybridization assays may be enhanced through use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBA TM, Cangene, Mississauga, Ontario) and Q Beta Replicase systems.

PCR is a template dependent DNA polymerase primer extension method of replicating select sequences of DNA. The method relies upon the use of an excess of specific primers to initiate DNA polymerass replication of specific subsequences of a DNA polynucleotide followed by repeated denaturation and polymerase extension steps. The PCR system is well known in the art (see U.S. Pat. Nos. 4,683,195 and 4,683,202). For additional information regarding PCR methods, see also, PCR Protocols: A Guide to Methods and Applications, ed. Innis, Gelland, Shinsky and White, Academic Press, Inc. (1990). Reagents and hardware for conducting PCR are available commercially through Perkin-Elmer/Cetus Instruments of Norwalk, Conn.

LCR, like PCR, uses multiple cycles of alternating temperature to amplify the numbers of a targeted sequence of DNA. LCR, however, does not use individual nucleotides for template extension. LCR relies instead upon an excess of oligonucleotides which are complementary to both strands of the target region. Following the denaturation of a double stranded template DNA, the LCR procedure begins with the ligation of two oligonucleotide primers complementary to adjacent regions on one of the target strands. Oligonucleotides complementary to either strand can be joined. After ligation and a second denaturation step, the original template strands and the two newly joined products serve as templates for additional ligation to provide an exponential amplification of the targeted sequences. This method has been detailed in Genomics, 4:560–569 (1989), which is incorporated herein by reference. As other amplification systems are developed, they may also find use in this invention.

The hybridization media and processes of the present invention, however, are uniquely suited to a one-step assay. The media may be pre-prepared, either commercially or in the laboratory to contain all the necessary components for hybridization. For instance, in a sandwich assay the media could comprise a lactam, desired buffers and detergents, a capture nucleic acid bound to a solid support such as a microbead, and a signal nucleic acid. This media then need only be combined with the sample containing the target nucleic acid at the time the assay is to be performed. Once hybridization occurs the hybridization complex attached to the solid support may be washed and the extent of hybridization determined.

Sandwich assays are commercially useful hybridization assays for detecting or isolating nucleic acid sequences. Such assays utilize a "capture" nucleic acid covalently immobilized to a solid support and labelled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

Virtually any solid surface can be used as a support for hybridization assays, including metals and plastics. Two types of solid surfaces are generally available namely:

a) Membranes, polystyrene beads, nylon, teflon, polystyrene/latex beads, latex beads or any solid support possessing an activated carboxylate, sulfonate, phosphate or similar activatable group are suitable for use as solid surface substratum to which nucleic acids or oligonucleotides can be immobilized.

b) Porous membranes possessing pre-activated surfaces which may be obtained commercially (e.g., Pall Immunodyne Immunoaffinity Membrane, Pall BioSupport Division, East Hills, N.Y., or Immobilon Affinity membranes from Millipore, Bedford, Mass.) and which may be used to immobilize capture oligonucleotides. Microbeads, including magnetic beads, of polystyrene, teflon, nylon, silica or latex may be used.

Capture or signal nucleic acids for use in hybridization assays can be obtained from the entire sequence or portions thereof of an organism's genome, from messenger RNA, or from cDNA obtained by reverse transcription of messenger RNA. After isolation of genomic DNA or cDNA fragments, the fragments are typically inserted into a replication vector, such as lambda phage, pBR322, M13, or vectors containing the SP6 or T7 promoter and cloned as a library in a bacterial host. Following appropriate screening procedures, a recombinant vector with the desired probe insert is isolated and labelled as described below. The vector is then grown in a suitable host. The probe and its vector are purified from the host cells by cell lysis and nucleic acid extraction. Following isolation, the probe can be purified away from the vector by digestion with selected restriction enzymes and sequenced. Further isolation of the probe can be achieved by using gel electrophoresis or high pressure liquid chromatography.

Once the appropriate sequences are determined, DNA probes are preferably chemically synthesized using commercially available methods and equipment. For example, the solid phase phosphoramidite method can be used to produce short probes of between 15 and 50 bases and have a molecular weight of less than 16,000 daltons. (Caruthers et al., *Cold Spring Harbor Symp. Quant. Biol.*, 47:411–418 (1982), and Adams et al., *J. Am. Chem. Soc.*, 105:661 (1983).

When synthesizing a probe for a specific target, the choice of nucleotide sequence will determine the specificity of the test. For example, by comparing DNA sequences from several virus isolates, one can select a sequence for virus detection that is either type specific or genus specific. Comparisons of DNA regions and sequences can be achieved using commercially available computer programs.

The determination of the extent of hybridization may be done by any of the methods well-known in the art. If there is no detectable hybridization, the extent of hybridization is thus 0. Typically labelled signal nucleic acids are used to detect hybridization. Complementary nucleic acids or signal nucleic acids may be labelled by any one of several methods typically used to detect the presence of hybridized polynucleotides. The most common method of detection is the use of autoradiography with $^3$H, $^{125}$I, $^{35}$S $^{14}$C, or $^{32}$P-labelled probes or the like. The choice of radioactive isotope depends on research preferences due to ease of synthesis, varying stability, and half lives of the selected isotopes. Other labels include ligands which bind to labelled antibodies, fluorophores, chemiluminescent agents, enzymes, and antibodies which can serve as specific binding pair members for a labelled ligand. The choice of label depends on sensitivity required, ease of conjugation with the probe, stability requirements, and available instrumentation.

The choice of label dictates the manner in which the label is bound to the probe. Radioactive probes are typically made using commercially available nucleotides containing the desired radioactive isotope. The radioactive nucleotides can be incorporated into probes by several means such as by nick translation of double-stranded probes; by copying single-stranded M13 plasmids having specific inserts with the Klenow fragment of DNA polymerase in the presence of radioactive dNTP; by transcribing cDNA from RNA templates using reverse transcriptase in the presence of radioactive dNTP; by transcribing RNA from vectors containing SP6 promoters or T7 promoters using SP6 or T7 RNA polymerase in the presence of radioactive rNTP; by tailing the 3′ ends of probes with radioactive nucleotides using terminal transferase; or by phosphorylation of the 5′ ends of probes using [$^{32}$P]-ATP and polynucleotide kinase.

Non-radioactive probes are often labelled by indirect means. Generally, a ligand molecule is covalently bound to the probe. The ligand then binds to an anti-ligand molecule which is either inherently detectable or covalently bound to a signal system, such as a detectable enzyme, a fluorescent compound, or a chemiluminescent compound. Ligands and anti-ligands may be varied widely. Where a ligand has a natural anti-ligand, for example, biotin, thyroxine, and cortisol, it can be used in conjunction with the labelled, naturally occurring anti-ligands. Alternatively, any haptenic or antigenic compound can be used in combination with an antibody.

Probes can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, AMPPD([3-(2′-spiroamantane)-4-methoxy-4-(3′phosphoryloxy)-phenyl-1,2-dioxetane]) and 2,3-dihydrophthalazinediones, e.g., luminol.

The amount of labelled probe which is present in the hybridization medium or extraction solution may vary widely. Generally, substantial excesses of probe over the stoichiometric amount of the target nucleic acid will be employed to enhance the rate of binding of the probe to the target DNA. Treatment with ultrasound by immersion of the reaction vessel into commercially available sonication baths can often times accelerate the hybridization rates.

After hybridization at a temperature and time period appropriate for the particular hybridization solution used, the glass, plastic, or filter support to which the capture nucleic acid-target nucleic acid hybridization complex is attached is introduced into a wash solution typically containing similar reagents (e.g., sodium chloride, buffers, organic solvents and detergent), as provided in the hybridization solution. These reagents may be at similar concentrations as the hybridization medium, but often they are at lower concentrations when more stringent washing conditions are desired. The time period for which the support is maintained in the wash solutions may vary from minutes to several hours or more.

Either the hybridization or the wash medium can be stringent. After appropriate stringent washing, the correct hybridization complex may now be detected in accordance with the nature of the label.

The probe may be conjugated directly with the label. For example, where the label is radioactive, the probe with associated hybridization complex substrate is exposed to X-ray film. Where the label is fluorescent, the sample is detected by first irradiating it with light of a particular wavelength. The sample absorbs this light and then emits light of a different wavelength which is picked up by a detector (*Physical Biochemistry*, Freifelder, D., W. H. Freeman & Co. (1982), pp. 537–542). Where the label is an enzyme, the sample is detected by incubation on an appropriate substrate for the enzyme. The signal generated may be a colored precipitate, a colored or fluorescent soluble material, or photons generated by bioluminescence or chemi-luminescence. The preferred label for probe assays generates a colored precipitate to indicate a positive reading. For example, alkaline phosphatase will dephosphorylate indoxyl phosphate which then will participate in a reduction reaction to convert tetrazolium salts to highly colored and insoluble formazans.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label. (Tijssen, P., "Practice and Theory of Enzyme Immunoassays," *Laboratory Techniques in Biochemistry and Molecular Biology*, Burdon, R. H., van Knippenberg, P.H., Eds., Elsevier (1985), pp. 9–20.)

In regard to the isolation of RNA, we have also discovered that the common and preferred use of a chaotropic agent, such as a salt of isothiocyanate (e.g., guanidine thiocyanate) does not provide for the complete disruption of protein and nucleic acid interactions, thus, preventing optimal hybridization. A significant and surprising increase in hybridization does occur when heat is applied to the hybridization solution containing the chaotropic agent and target nucleic acid. Previously, researchers have attempted to keep hybridization temperatures low to maintain stability of the reactants. See Cox et al., EP Application No. 84302865.5. Thus, it was surprising that heat would improve the sensitivity of the hybridization assay and do so so dramatically.

This invention also provides efficient methods for increasing the sensitivity of ribonucleic acid hybridization assays and for simplifying the steps of the assays. The processes for conducting nucleic acid hybridizations wherein the target nucleic acid is RNA comprise heating a nucleic acid solution or sample to a temperature of about 60°–100° C., preferably greater than 65° C. and most preferably to about 65°–70° C. The nucleic acid solution will comprise a chaotropic agent, a target nucleic acid, and a nucleic acid substantially complementary to the target nucleic acid of interest. The nucleic acid solution will be heated to fully disrupt the protein and nucleic acid interactions to maximize target nucleic acid hybridization. The heating time is preferably about 1 to 10 minutes, most preferably about 5 minutes for solutions containing about 0.001 to 1000 μg of nucleic acid per ml. The addition of the heating step increases the sensitivity of the hybridization assays regardless of whether lactams are included. The solution is then cooled until the complementary nucleic acid has hybridized with the target nucleic acid to form a hybridization complex. The cooling process and rate of cooling are not critical. Cooling may be achieved by simply allowing the solution to cool to room temperature.

These methods are additionally advantageous because they allow for minimal handling of the samples and assay reagents. A prepared reagent solution may be provided, for example, which would contain a chaotropic agent, other appropriate components such as buffers or detergents, a capture nucleic acid bound to a solid support, and a signal nucleic acid, both capable of hybridizing with a target nucleic acid. Conveniently, a complex biological sample suspected of harboring a target nucleic acid can be directly combined with the pre-prepared reagent for hybridization, thus, allowing the hybridization to occur in one step. The combined solution is heated as described herein and then cooled until hybridization has occurred. The resulting hybridization complex is then simply washed to remove unhybridized material and the extent of hybridization is determined.

Kits for the extraction of and hybridization of nucleic acids are also contemplated. Such kits would contain at least one vial containing an extraction solution or a hybridization medium which comprises a lactam at a concentration in excess of 5%. Detergents, buffer solutions and additional vials which contain components to detect target nucleic acids may also be included.

The following examples are offered by way of illustration and are not to be construed as limiting the invention, as claimed, in any way.

EXAMPLE I: Lysis of bacterial and human cells with pyrrolidone-based solutions.

A pre-prepared lysis solution composed of 20% N-cyclohexyl-2-pyrrolidone, and 20% N-hydroxymethyl-2-pyrrolidone, (both obtained from GAF Chemicals Corporation, Wayne, N.J.), 50 mM Tris, pH 7.6, 25 mM EDTA, and 2% SDS (sodium dodecyl sulfate) was used to lyse $1 \times 10^9$ cells of Actinobacillus actinomycetecomitans ("Aa"), Bacteroides intermedius ("Bi"), Eikenella corrodens ("Ec"), Wolinella recta ("Wr"), Fusobacterium nucleatum ("Fn"), Bacteroides gingivalis ("Bg"), and $1 \times 10^6$ cells of HeLa in 100 microliter volumes each. The solution was noted to clear within 10 seconds and phase contrast microscopy indicated the solubilization of all the cell types tested. No intact cell shapes were observed by light microscopy. In addition, the lysates were observed by fluorescence microscopy in which ethidium bromide was added to the lysate at a concentration of 0.5 micrograms per ml. Only extremely diffuse staining was observed in all lysates compared to intact cell controls, indicating that lysis was complete and that chromosomal DNA was unfolded and released from the cells.

EXAMPLE II: Lysis of bacterial and human cells with pyrrolidone-based solutions containing a chaotropic agent.

A lysis solution composed of 20% N-cyclohexyl-2-pyrrolidone, 20% N-hydroxymethyl-2-pyrrolidone, 10% N-dodecyl-2-pyrrolidone, 1M Guanidine-HCl, 50 mM Tris, pH 7.6, 25 mM EDTA, and 2% SDS was used to lyse $1 \times 10^9$ cells of Aa, Bi, Ec, Wr, Fn, Bg, and $1 \times 10^6$ cells of HeLa in 100 microliter volumes. The solution was noted to clear within 10 seconds and phase contrast microscopy indicated the solubilization of all the cell types tested. No intact cell shapes were observed by light microscopy. In addition, the lysates were observed by fluorescence microscopy in which ethidium bromide was added to the lysate at a concentration of 0.5 micrograms per ml. Only extremely diffuse staining was observed in all lysates compared to intact cell controls, indicating that lysis was complete and that chromosomal DNA was unfolded and released from the cells.

EXAMPLE III: Combination pyrrolidone-based hybridization solutions promote specific nucleic acid base pairing.

A solution composed of 20% N-cyclohexyl-2-pyrrolidone, 20% N-hydroxymethyl 2-pyrrolidone, 50 mM Tris pH 7.6, 25 mM EDTA and 1% SDS was used to test the ability of $^{32}$P-labelled specific oligonucleotide probes (synthetic oligonucleotide probes in which the sequence is complementary to unique hypervariable regions of the 16s rRNA of the respective bacterium) to hybridize specifically to total nucleic acid from Aa, Bg, Bi, Ec, Fn, Wr and E. coli immobilized on Nytran filters (Schleicher and Schuell, Keene, N.H.). Approximately 50 nanograms of total nucleic acid was immobilized on each nytran slot. $6.5 \times 10^6$ cpm of $^{32}$P-labelled probe (approximately 65 nanograms) of Aa complementary probe (Aa4B) was added to 1 ml of the solution described above and incubated with nytran filter strips containing Aa, Bg, Bi, Ec, Fn, Wr, and E. coli slots of nucleic acid. Hybridization was allowed to proceed for 3 hours at 19° C. The filters were washed with 0.09M NaCl, 50 mM Tris pH 7.6, 25 mM EDTA and 0.1% SDS at 50° C. and radioactivity was then detected by fluorometry. Results indicated that the Aa probes hybridized only with Aa total nucleic acid, demonstrating that the pyrrolidone solution promoted specific nucleic acid base pairing. Identical results were obtained using solutions of the same composition described above with the exception of altering each pyrrolidone concentration to 15% or 25% respectively.

EXAMPLE IV: Individual pyrrolidone-based hybridization solutions promote specific nucleic acid base pairing.

A solution composed of 40% N-cyclohexyl-2-pyrrolidone, or 40% N-hydroxymethyl-2-pyrrolidone, or 40% N-methyl-2-pyrrolidone, 50 mM Tris pH 7.6, 25 mM EDTA and 1% SDS was used to test the ability of $^{32}$P-labelled specific oligonucleotide probes (synthetic oligonucleotide probes in which the sequence is complementary to unique hypervariable regions of the 16s rRNA of the respective bacterium) to hybridize specifically to total nucleic acid from Aa, Bg, Bi, Ec, Fn, Wr, and E. coli immobilized on Nytran filters. Approximately 50 nanograms of total nucleic acid was immobilized on each nytran slot. $6.5 \times 10^6$ cpm of $^{32}$P-labelled probe (approximately 65 nanograms) of Aa complementary probe (Aa4B) was added to 1 ml of the solution described above and incubated with nytran filter strips containing Aa, Bg, Bi, Ec, Fn, Wr, and E. coli slots of nucleic acid. Hybridization was allowed to proceed for 3 hours at 19° C. The filters were washed with 0.09M NaCl, 50 mM Tris pH 7.6, 25 mM EDTA and 0.1% SDS (SDS/FW) at 50° C. and radioactivity was then detected by fluorometry. Results indicated that the Aa probes hybridized only with Aa total nucleic acid demonstrating that the individual pyrrolidone solutions promoted specific nucleic acid base pairing. Identical results were obtained using solutions of the same composition described above with the exception of altering the individual pyrrolidone concentration to 30% or 50%, respectively.

EXAMPLE V: Individual pyrrolidone-based hybridization solutions containing chaotropic agents, piperidone based hybridization solutions and caprolactam or valerolactam-based hybridization solutions promote specific nucleic acid base pairing.

A solution composed of 35% N-methyl-2-piperidone, or 35% 2-ε-caprolactam, or 35% N-methyl-2-caprolactam, or 35% 2-δ-valerolactam, 50 mM Tris pH 7.6, 25 mM EDTA and 1% SDS or a solution containing 20% N-cyclohexyl-2-pyrrolidone, 20% N-hydroxyethyl-2-pyrrolidone, 5% N-dodecyl-2-pyrrolidone, 1M guanidine-HCl, 50 mM Tris pH 7.6, 25 mM EDTA and 2% SDS, or a solution containing 20% N-cyclohexyl-2-pyrrolidone, 20% N-hydroxyethyl-2-pyrrolidone, 5% N-dodecyl-2-pyrrolidone, 0.5M guanidine HCl, 50 mM Tris pH 7.6, 25 mM EDTA and 2% SDS, was used to test the ability of $^{32}$P-labelled specific oligonucleotide probes (synthetic oligonucleotide probes in which the sequence is complementary to unique hypervariable regions of the 16s rRNA of the respective bacterium) to hybridize specifically to total nucleic acid from Aa, Bg, Bi, Ec, Fn, Wr, and *E. coli* immobilized on Nytran filters. Approximately 50 nanograms of total nucleic acid was immobilized on each nytran slot. $6.5 \times 10^6$ cpm of $^{32}$P-labelled probe (approximately 65 nanograms) of Bg complementary probe (BgSB) was added to 1 ml of the solution described above and incubated with nytran filter strips containing Aa, Bg, Bi, Ec, Fn, Wr, and *E. coli* slots of nucleic acid. Hybridization was allowed to proceed for 3 hours at 19° C. The filters were washed with 0.09M NaCl, 50 mM Tris pH 7.6, 25 mM EDTA and 0.1% SDS (SDS/FW) at 19° C. and radioactivity was then detected by fluorometry. Results indicated that the Bg probes hybridized only with the Bg total nucleic acid demonstrating that the individual piperidone or lactam-based hybridization solutions promoted specific nucleic acid base pairing.

EXAMPLE VI: Specific detection of Bg bacterium in pyrrolidone-based hybridization media.

A hybridization media composed of 20% N-cyclohexyl-2-pyrrolidone, and 20% N-hydroxymethyl-2-pyrrolidone, 50 mM Tris, pH 7.6, 25 mM EDTA, and 2% SDS was used to lyse $1 \times 10^8$ cells of Aa, Bi, Ec, Wr, Fn, or Bg in 100 microliter volumes at 19° C. Biotinylated 24-mer oligonucleotide probes complementary to conserved regions of bacterial 16s rRNA (target probes) were added to a final concentration of 100 nanograms per ml. This solution was then incubated with nytran discs which had covalently immobilized 1 microgram of Bg specific oligonucleotide probe (capture probe) for 1 hour at ambient temperature. The solid supports were then washed with SDS/FW at ambient temperature and then incubated with 10 ng/ml of Strepavidin/Horseradish peroxidase (SA/HRP) conjugate in SDS/FW for 30 minutes at ambient temperature. The solid supports were then washed with SDS/FW, FW (filtered water), and then the presence of peroxidase was determined by incubating the filter with a substrate that formed an insoluble product. The results indicated that only the Bg bacterium was detected in the colorimetric sandwich assay. The pyrrolidone hybridization media therefore promoted effective lysis and specific nucleic acid base pairing of the target nucleic acid.

EXAMPLE VII: Purification of total nucleic acid or DNA from bacterial cells solubilized with 3M GnSCN.

To recover total nucleic acid from GnSCN-solubilized bacterial cells approximately $1 \times 10^9$ Bg cells were lysed in 100 microliters of 3M GnSCN, 50 mM Tris pH 7.6, 25 mM EDTA and 2% Sarkosyl. An equivalent of N-methyl-2-pyrrolidone was added (100 microliters) followed by 500 microliters of phenol and 300 microliters of 1% SDS, 50 mM Tris pH 7.6, 25 mM EDTA and 0.05M NaCl. The solution was then heated to 65° C. for 10 minutes and then mixed for 3 minutes at ambient temperature. The solution was then subjected to centrifugation at 10,000 rpm for 5 minutes to force phase separation. The upper aqueous phase was then decanted and nucleic acid was precipitated with 2 volumes of 100% ethanol. Nucleic acid was pelleted for 5 minutes at 10,000 rpm at ambient temperature and the resulting pellet was solubilized with 100 microliters of water. An aliquot was examined by gel electrophoresis. The results indicate that chromosomal DNA, and rRNA was efficiently extracted from the GnSCN solubilized bacterial cells.

EXAMPLE VIII: The sequential isolation of DNA and rRNA from bacterial cell solubilized with 3M GnSCN.

To recover DNA and rRNA sequentially from GnSCN-solubilized bacterial cells approximately $1 \times 10^9$ Bg cells were lysed in 100 microliters of 3M GnSCN, 50 mM Tris pH 7.6, 25 mM EDTA and 2% Sarkosyl. An equivalent of N-methyl-2-pyrrolidone was added (100 microliters) followed by 500 microliters of phenol and 300 microliters of 1% SDS, 50 mM Tris pH 7.6, 25 mM EDTA and 0.05M NaCl. The solution was mixed for 3 minutes at ambient temperature and then subjected to centrifugation at 10,000 rpm for 5 minutes to force phase separation. The upper aqueous phase was then decanted and nucleic acid was precipitated with 2 volumes of 100% ethanol. Another 300 microliters of 1% SDS, 50 mM Tris, 25 mM EDTA and 0.05M NaCl was added to the organic (lower phase) and the solution was then heated to 65° C. for 10 minutes and then mixed for 3 minutes at ambient temperature. Again, the nucleic acid in the upper aqueous phase was precipitated by the addition of two volumes of 100% ethanol. Nucleic acid was pelleted for 5 minutes at 10,000 rpm at ambient temperature and the resulting pellet was solubilized with 100 microliters of water. An aliquot was examined by gel electrophoresis. The results indicate that first chromosomal DNA was recovered from the GnSCN lysate followed by the recovery of rRNA. Both nucleic acid types were efficiently extracted and purified from the GnSCN solubilized bacterial cells. This procedure permits the recovery and separation of DNA and rRNA from cells solubilized with chaotropic salts such as GnSCN.

EXAMPLE IX: Recovery of plasmid DNA from bacterial cells partially solubilized with guanidine-HCl.

Bacterial cells such as *E. coli* can be partially solubilized with weak chaotropic salt solutions such as guanidine-HCl which contain non-ionic detergents. Partially solubilized cells leak RNA and plasmid DNA while retaining chromosomal DNA. These observations were used to develop a method for the rapid and simple isolation of plasmid DNA from *E. coli*.

Approximately $1 \times 10^9$ *E. coli* cells transfected with PBR 322 plasmid were partially solubilized with 100 microliters of 2M guanidine-HCl, 50 mM Tris, 25 mM EDTA and 2% Sarkosyl. The cells were incubated without agitation for 2 minutes at ambient temperature. After the incubation cells and insoluble material was pelleted at 10,000 rpm for 1 minute and the supernatant was decanted and reserved. To the supernatant 100 microliters of N-methyl-2-pyrrolidone was added followed by 500 microliters of phenol and 300 microliters of SDS-extraction buffer.

The solution was mixed for 3 minutes at ambient temperature and the solution was then subjected to centrifugation at 10,000 rpm for 5 minutes to force phase separation. The upper aqueous phase was then decanted and nucleic acid was precipitated with 2 volumes of 100% ethanol. Nucleic acid was pelleted for 5 minutes at 10,000 rpm at ambient temperature and the resulting pellet was solubilized with 100 microliters of water. An aliquot was examined by gel electrophoresis. The results indicate that relative to total extracted nucleic acid, plasmid DNA was preferentially extracted, essentially free of chromosomal DNA, rRNA and protein.

EXAMPLE X: Extraction and immobilization of total nucleic acid from bacterial cells onto solid supports for the detection of pathogens in complex biological samples using oligonucleotide probes.

To recover total nucleic acid from GnSCN-solubilized bacterial cells a combination of approximately $1 \times 10^8$ Aa, Bg, Bi, Ek, Fn, Wr cells were lysed in 100 microliters of 3M GnSCN, 50 mM Tris pH 7.6, 25 mM EDTA and 2% Sarkosyl. An equivalent of N-methyl-2-pyrrolidone was added (100 microliters) followed by 500 microliters of phenol and 300 microliters of 1% SDS, 50 mM Tris pH 7.6, 25 mM EDTA and 0.05M NaCl. The solution was then heated to 65° C. for 10 minutes and then mixed for 3 minutes at ambient temperature. The solution was then subjected to centrifugation at 10,000 rpm for 5 minutes to force phase separation. 20 microliter portions of the upper aqueous phase were then slotted into Nytran filters using a slotting apparatus.

The filters were then heated to 95° C. for 3 hours. Approximately 50 nanograms of total nucleic acid was immobilized on each nytran slot. $6.5 \times 10^6$ cpm of $^{32}$P-labelled probe (approximately 65 nanograms) of either Aa, Bg, Bi, Ek, Fn, or Wr complementary probe was added to 1 ml of the pyrrolidone-based hybridization solution described above and incubated with nytran filter strips containing Aa, Bg, Bi, Ec, Fn, Wr, and E. coli slots of nucleic acid. Hybridization was allowed to proceed for 3 hours at 19° C. The filters were washed with 0.09M NaCl, 50 mM Tris pH 7.6, 25 mM EDTA and 0.1% SDS (SDS/FW) at ambient temperature and radioactivity was then detected by fluorometry. Results indicated that the specific probes hybridized only with their respective total nucleic acid indicating that target nucleic acid can be directly immobilized onto a solid support after extraction of chaotropic salts containing solubilized nucleic acid with lactam-based solutions.

EXAMPLE XI: The use of pyrrolidones to isolate total nucleic acid from bacterial cells without the use of phenol.

A pre-prepared lysis solution composed of 20% N-cyclohexyl-2-pyrrolidone, 20% N-hydroxymethyl-2-pyrrolidone, 10% N-dodecyl-2-pyrrolidone, 50 mM Tris, pH 7.6, 25 mM EDTA, and 2% SDS was used to lyse $1 \times 10^9$ cells of Aa, Bi, Ec, Wr, Fn, Bg, and $1 \times 10^6$ cells of HeLa in 100 microliter volumes. An equal volume of N-methyl-2-pyrrolidone was then added followed by the addition of 200 microliters of N-dodecyl-2-pyrrolidone. The solution immediately became biphasic.

The solution was mixed for 3 minutes at ambient temperature and the solution was then subjected to centrifugation at 10,000 rpm for 5 minutes to force phase separation. The upper aqueous phase was then decanted and nucleic acid was precipitated with 2 volumes of 100% ethanol. Nucleic acid was pelleted for 5 minutes at 10,000 rpm at ambient temperature and the resulting pellet was solubilized with 100 microliters of water. An aliquot was examined by gel electrophoresis. The results indicate that total nucleic acid was preferentially extracted and purified from the cell lysate.

Example XII: One step assay to detect specific nucleic acid sequences of bacterial pathogens.

A pre-prepared lysis solution composed of 20% N-cyclohexyl-2-pyrrolidone, 20% N-hydroxymethyl-2-pyrrolidone, 10% N-dodecyl-2-pyrrolidone, 50 mM Tris, pH 7.6, 25 mM EDTA, and 2% SDS and containing 1 to 5 mg of 5 micron beads (silica, (Spherisorb) from Phase Sep, Deeside Ind., Queensferry, Clwyd, U.K.) onto which 1 to 2 micrograms of Bg specific oligonucleotide probe has been covalently immobilized, and which also contained $1 \times 10^6$ cpm of $^{32}$P oligonucleotide probe (specific activity of $1 \times 10^7$ cpm per microgram) complementary to Bg specific regions of the 16s rRNA was used to lyse $1 \times 10^6$ cells of Aa, Bi, Ec, Wr, Fn, and Bg in 100 microliter volumes at 19° C. The solution was then incubated for 30 minutes at room temperature. The solid supports were then washed with SDS/FW at ambient temperature to remove un-hybridized material and radioactive probes. The solid supports were then monitored for radioactivity by scintillation counting. The results indicated that only Bg cells were detected when using Bg specific oligonucleotide signal probes and not when using specific labelled probes for Aa, Bi, Ek, Fn or Wr. Thus, in 30 minutes $1 \times 10^6$ Bg cells were detected in a simple one step hybridization assay.

EXAMPLE XIII: Detection of Bg specific nucleotide sequences in heated GnSCN lysate using a colorimetric sandwich assay format.

A lysis solution composed of 3M GnSCN, 2% Sarkosyl, 50 mM Tris, pH 7.6, 25 mM EDTA was used to lyse two sets of $1 \times 10^8$ cells of Bg in 100 microliter volumes at 19° C. One set was then heated in a 65° C. water bath for 10 minutes while the other set remained at room temperature for the same period of time. Biotinylated 24-mer oligonucleotide probes complementary to conserved regions of bacterial 16s rRNA (signal probes) were added to a final concentration of 100 nanograms per ml to both the lysate and to the 3M GnSCN lysing solution that was to be used as the diluent. Seven, tenfold serial dilutions were then made with both the heated and unheated lysate and then these solutions were incubated with nytran discs which had covalently immobilized 1 microgram of Bg specific oligonucleotide probe (capture probe) for 1 hour at ambient temperature. The solid supports were then washed with SDS/FW (sodium dodecyl sulfate and filtered water) at ambient temperature and then incubated with 10 ng/ml of Strepavidin/Horseradish peroxidase (SA/HRP) conjugate in SDS/FW for 30 minutes at ambient temperature. The solid supports were then washed with SDS/FW,FW (filtered water), and then the presence of peroxidase was determined by incubating the filter with a substrate that formed an insoluble product. The results indicated that a level of sensitivity of $1 \times 10^6$ bacterial cells was achieved using the heated GnSCN lysate and that a level of sensitivity of $1 \times 10^7$ bacterial cells was achieved using the unheated GnSCN lysate. Thus, heating the lysate to a temperature above 60° C. for at least 10 minutes increased the sensitivity of the assay by at least ten-fold.

What is claimed is:

1. A composition for simultaneously lysing cells and hybridizing released endogenous nucleic acid, comprising:
   a buffer solution;
   at least one monomeric lactam at a concentration of about 5% to about 70% of the total volume of the buffer solution; and
   a detergent at a concentration of about 0.05% to about 0.5%.

2. The composition of claim 1 further comprising a chaotropic agent.

3. The composition of claim 1 further comprising about 1 to about 10 mM EDTA.

4. The composition of claim 1 further comprising a volume exclusion agent.

5. A kit for simultaneously lysing cells and hybridizing released endogenous nucleic acid, comprising at least one vial containing a composition comprising:
   a buffer solution;
   at least one monomeric lactam at a concentration of about 5% to about 70% of the total volume of the buffer solution; and
   a detergent at a concentration of about 0.05% to about 0.5%.

* * * * *